US012584900B2

(12) United States Patent
Sano

(10) Patent No.: US 12,584,900 B2
(45) Date of Patent: Mar. 24, 2026

(54) METHOD, KIT, AND SENSOR FOR DETECTING ANTIBODY OF INTEREST IN WASTEWATER

(71) Applicant: TOHOKU UNIVERSITY, Miyagi (JP)

(72) Inventor: Daisuke Sano, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 18/119,403

(22) Filed: Mar. 9, 2023

(65) Prior Publication Data

US 2023/0375519 A1 Nov. 23, 2023

(30) Foreign Application Priority Data

Mar. 15, 2022 (JP) ................................. 2022-040763

(51) Int. Cl.
*G01N 33/18* (2006.01)
*G01N 27/327* (2006.01)

(52) U.S. Cl.
CPC ..... *G01N 33/1826* (2013.01); *G01N 27/3277* (2013.01); *G01N 33/1886* (2013.01)

(58) Field of Classification Search
CPC .......... G01N 33/1826; G01N 27/3277; G01N 33/1886
See application file for complete search history.

(56) References Cited

U.S. PATENT DOCUMENTS

| | | | |
|---|---|---|---|
| 2016/0054311 A1* | 2/2016 | Marks ................ | G01N 33/5438 204/403.01 |
| 2021/0102912 A1* | 4/2021 | Park ..................... | G01N 27/301 |
| 2022/0003766 A1* | 1/2022 | Wohlstadter .......... | C12Q 1/701 |

FOREIGN PATENT DOCUMENTS

| | | |
|---|---|---|
| JP | 2017-524137 | 8/2017 |
| KR | 20220013928 A * | 2/2022 |
| WO | 2016/025153 | 2/2016 |

OTHER PUBLICATIONS

Holzer et al., "Characterization of Covalently Bound Anti-Human Immunoglobulins on Self-Assembled Monolayer Modified Gold Electrodes", Adv. Biosys., 2017, vol. 1, 1700055.
Kitajima et al., "Development of a MEMS-based electrochemical aptasensor for norovirus detection", Micro & Nano Letters, 2016, vol. 11, Issue 10, pp. 582-585.
Hirano et al., "Improvement of Electrochemical Conditions for Detecting Redox Reaction of K3 [Fe(CN)6] toward the Application in Norovirus Aptasensor", Electrochemistry, 2020, vol. 88, No. 3, pp. 205-209.
Lu et al., "Prospects and challenges of using electrochemical immunosensors as an alternative detection method for SARS-CoV-2 wastewater-based epidemiology", Science of the Total Environment, vol. 777, 2021, 146239.

* cited by examiner

*Primary Examiner* — Feba Pothen

(74) *Attorney, Agent, or Firm* — Wenderoth, Lind & Ponack, L.L.P.

(57) ABSTRACT

A method of detecting an antibody of interest in wastewater includes: bringing an electrode, modified with a protein that specifically binds with the antibody of interest, into contact with the wastewater; bringing the electrode into contact with a reaction solution containing a redox substance; and applying a voltage to the electrode in a state of being in contact with the reaction solution, and measuring a current.

10 Claims, 4 Drawing Sheets

METHOD, KIT, AND SENSOR FOR DETECTING ANTIBODY OF INTEREST IN WASTEWATER

CROSS-REFERENCE TO RELATED APPLICATION

This application claims priority from Japanese Patent Application No. 2022-040763, filed on Mar. 15, 2022, the entire disclosure of which is incorporated herein by reference.

BACKGROUND OF THE INVENTION

1. Field of the Invention

Cross-Reference to Related Application

The present invention relates to a method, kit, and sensor for detecting an antibody of interest in wastewater.

2. Description of the Related Art

In recent years, as a measure against a viral infectious disease that causes significant harm to society, a wastewater-based epidemiological approach involving early detection of the occurrence of an infectious disease patient and an outbreak of infection through utilization of epidemiological information contained in municipal wastewater has been attracting attention. At present, wastewater-based epidemiological surveillance concerning an infectious disease mainly targets a viral gene and is performed through detection thereof by quantitative PCR. However, there are problems in, for example, that it takes time to detect/quantify a viral gene from a collected wastewater sample, that the sample needs to be concentrated because of a low virus concentration, and that analysis entails a huge cost and manpower burden. It is strongly desired that the problems be solved.

SUMMARY OF THE INVENTION

An object of the present invention is to provide a novel method by which an antibody of interest in a wastewater sample can be detected in a simple manner.

Under such circumstances, the inventors of the present invention have made extensive investigations, and as a result, have focused on an antiviral antibody discharged at a high concentration as compared to a virus itself as an infectious disease-related marker in wastewater, and have made an attempt to establish a detection method therefor. Then, the inventors of the present invention have found, after a great deal of trial and error, that the above-mentioned object can be achieved by bringing an electrode modified with a protein that specifically binds with the antibody of interest into contact with wastewater, and then applying a voltage to the electrode and measuring a current under a state in which the electrode is brought into contact with a reaction solution containing a redox substance. The present invention is based on the above-mentioned novel finding. Accordingly, the present invention provides the following items:

Item 1. A method of detecting an antibody of interest in wastewater, the method including: a step of bringing an electrode modified with a protein that specifically binds with the antibody of interest into contact with wastewater; a step of bringing the electrode brought into contact with the wastewater in the preceding step into contact with a reaction solution containing a redox substance; and a step including applying a voltage to the electrode in a state of being brought into contact with the reaction solution, and measuring a current.

Item 2. The method according to Item 1, wherein the antibody of interest is one of an antiviral antibody, an antibacterial antibody, an antiprotozoal antibody, or an anti-tumor cell antibody.

Item 3. The method according to Item 1 or 2, wherein the protein that specifically binds with the antibody of interest is one of an antibody that specifically binds to the antibody of interest or an antigen protein to which the antibody of interest specifically binds.

Item 4. The method according to any one of Items 1 to 3, wherein the electrode is modified with the protein that specifically binds with the antibody of interest via a self-assembled monolayer.

Item 5. The method according to any one of Items 1 to 4, wherein the redox substance is at least one kind selected from the group consisting of: a hexacyanidoferrate(II) ion and/or a hexacyanidoferrate(III) ion; an EDDHA-iron complex; a DTPA-iron complex; and salts thereof.

Item 6. A kit for detecting an antibody of interest in wastewater by the method of any one of Items 1 to 5, the kit including an electrode modified with a protein that specifically binds with the antibody of interest.

Item 7. A sensor for detecting an antibody of interest in wastewater by the method of any one of Items 1 to 5, the sensor including: a working electrode modified with a protein that specifically binds with the antibody of interest; and a counter electrode.

Item 8. An analysis system configured to detect an antibody of interest in wastewater by the method of any one of Items 1 to 5.

Item 9. The analysis system according to Item 8, wherein the analysis system is configured to measure a concentration of the antibody of interest in a wastewater sample in real time.

According to the present invention, the novel method by which an antibody of interest in a wastewater sample can be detected in a fast and simple manner can be provided.

DESCRIPTION OF THE EMBODIMENTS

Figure 1:
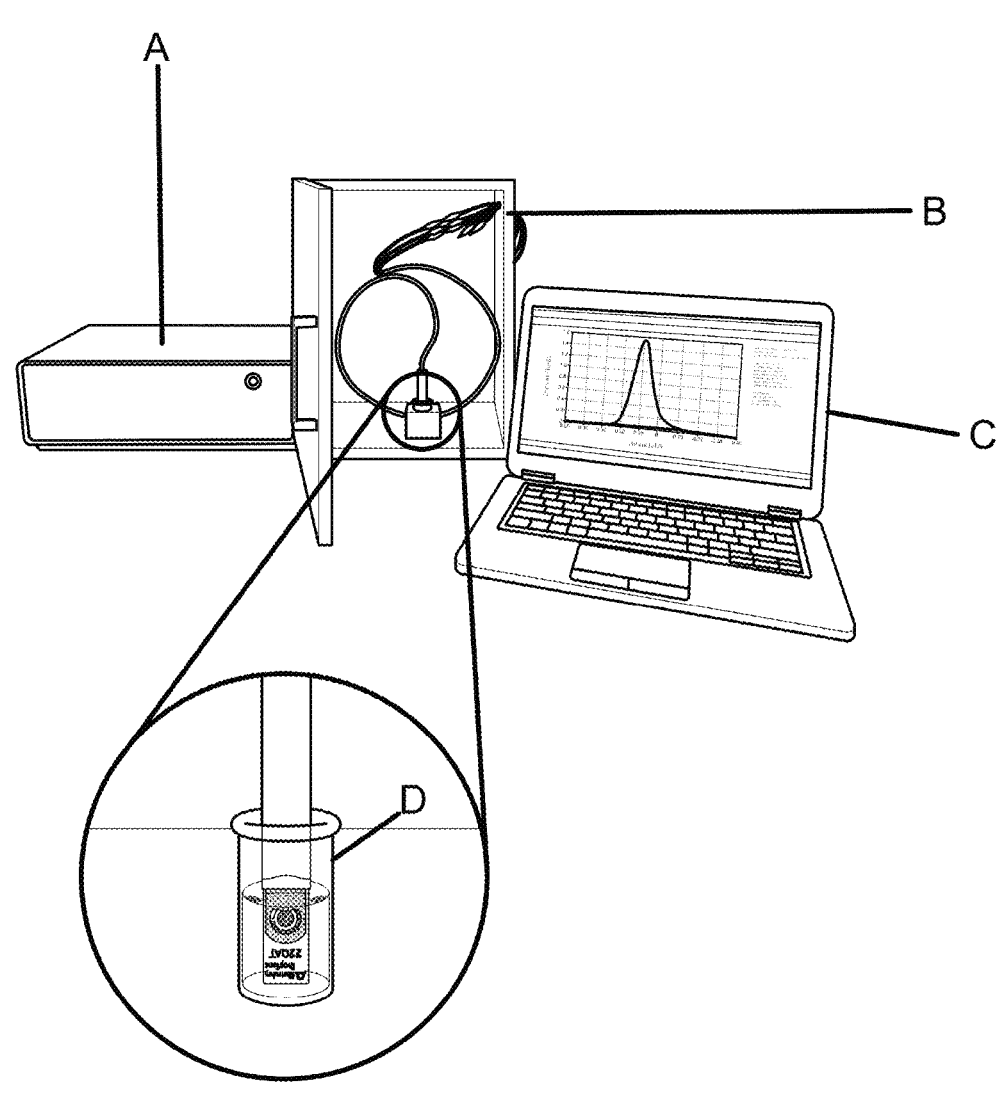
FIG. 1 shows an overview example of an electrochemical analyzer system used for the detection of a human antibody in wastewater in Example.

As used herein, singular forms (e.g., "a", "an", and "the") include singular and plural referents, unless otherwise indicated herein or clearly contradicted by context.

In at least one embodiment of the present invention, the terms "protein" and "peptide" are each used in a meaning including an oligopeptide and a polypeptide. In addition, as used herein, the terms "protein" and "peptide" each encompass both of a protein modified with a glycan or the like and an unmodified protein, unless otherwise stated. The same applies to a protein that is not specified to be a protein.

Method of Detecting Antibody of Interest

According to at least one embodiment of the present invention, there is provided a method of detecting an antibody of interest in wastewater, the method including: a step of bringing an electrode modified with a protein that specifically binds with the antibody of interest into contact with wastewater; a step of bringing the electrode brought into contact with the wastewater in the preceding step into contact with a reaction solution containing a redox substance; and a step including applying a voltage to the electrode in a state of being brought into contact with the reaction solution, and measuring a current.

The antibody of interest is not particularly limited, and examples thereof include an antiviral antibody, an antibacterial antibody, an antiprotozoal antibody, and an anti-tumor cell antibody. A virus to be targeted is also not particularly limited, and examples thereof include influenza viruses, coronaviruses (including SARS-CoV-2), noroviruses, the hepatitis A virus, and dengue virus. The method according to at least one embodiment of the present invention is useful because, instead of a protein that a virus, a bacterium, or the like itself has, an antibody produced by an animal infected with such virus, bacterium, or the like is detected, to thereby suggest not only the presence of the virus, the bacterium, or the like in a locality where a wastewater sample was acquired, but also the presence of a patient infected with the virus, the bacterium, or the like.

Examples of the antibody include antibodies derived from mammals, such as a human, a mouse, a dog, a cat, a bovine, and a horse. In addition, examples of the antibody include immunoglobulins, such as IgA, IgG, IgM, IgD, and IgE.

In this embodiment, first, the step of bringing an electrode modified with a protein that specifically binds with the antibody of interest into contact with wastewater is performed. In at least one embodiment of the present invention, examples of the protein that specifically binds with the antibody of interest include not only an antibody that specifically binds to the antibody of interest, but also an antigen protein to which the antibody of interest specifically binds. For example, antibodies that specifically bind to the above-mentioned antibodies may be widely used as the antibody that specifically binds to the antibody of interest, and examples thereof include an anti-IgA antibody, an anti-IgG antibody, an anti-IgM antibody, an anti-IgD antibody, and an anti-IgE antibody. Examples of the antibody that specifically binds to the antibody of interest include: an antibody that specifically binds to a constant region of the antibody of interest; and an antibody that specifically binds to a variable region of the antibody of interest. In addition, examples of the antibody that specifically binds to the antibody of interest include antibodies derived from mammals, such as a human, a mouse, a dog, a cat, a bovine, and a horse. In addition, examples of the antibody that specifically binds to the antibody of interest include immunoglobulins, such as IgA, IgG, IgM, IgD, and IgE.

The antigen protein to which the antibody of interest specifically binds is not particularly limited, but for example, when the antibody of interest is an antiviral antibody, examples of the antigen protein to which the antibody of interest specifically binds include the nucleocapsid protein (N protein) of SARS-CoV-2, the spike protein (S protein) of SARS-CoV-2, a capsid protein of a norovirus, a capsid protein of the hepatitis A virus, the E protein of dengue virus, and polypeptides formed of partial sequences of those proteins.

Figure 4:
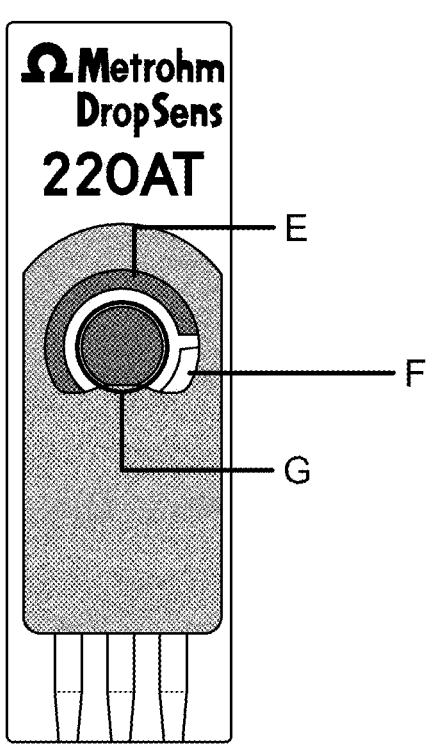
FIG. 4 shows an outline of an example of arrangement of a working electrode, a reference electrode, and a counter electrode in at least one embodiment of the present invention. E: counter electrode, F: reference electrode, G: working electrode.

In at least one embodiment of the present invention, the electrode modified with the protein that specifically binds with the antibody of interest is used as a working electrode. A material for such electrode is not particularly limited, and examples thereof include a gold electrode, a platinum electrode, a diamond electrode, a palladium electrode, and a carbon electrode. Of those, a gold electrode or the like is preferred. The shape of the working electrode is also not particularly limited, but examples thereof include a flat plate-shaped electrode and a porous electrode. Of those, a flat plate-shaped electrode is preferred. The area of the working electrode is also not particularly limited, but is, for example, from 1 mm$^2$ to 50 mm$^2$, preferably from 10 mm$^2$ to 20 mm$^2$. An example of the electrode is a product in which a working electrode, a reference electrode, and a counter electrode are arranged on one substrate. Specifically, for example, such a product as shown in FIG. 4 may be used.

A method of immobilizing the protein that specifically binds with the antibody of interest on the electrode is not particularly limited, and methods used in the technical field to which the present invention pertains may be widely used. An example thereof is a method involving modifying the electrode with the protein that specifically binds with the antibody of interest via a self-assembled monolayer (SAM). More specifically, as a raw material for the self-assembled monolayer, there is given, for example, a thioalkylcarboxylic acid. Examples of the thioalkylcarboxylic acid include 11-mercaptoundecanoic acid (MUA) and 3-mercaptopropionic acid (MPA). In at least one embodiment of the present invention, those thioalkylcarboxylic acids may be used alone or in combination thereof. In addition, in at least one embodiment of the present invention, the self-assembled monolayer is preferably activated in order to facilitate the bonding of the protein that specifically binds with the antibody of interest to the self-assembled monolayer. For example, in at least one embodiment of the present invention in which the thioalkylcarboxylic acid is used as the material for the self-assembled monolayer, a thiol group is bonded to the electrode to form a self-assembled monolayer having a terminal carboxyl group. In at least one embodiment of the present invention in which the thioalkylcarboxylic acid is used, it is preferred to activate the above-mentioned self-assembled monolayer having a carboxyl group in order to bond the protein that specifically binds with the antibody of interest to the self-assembled monolayer. As a compound to be used for the activation of the self-assembled monolayer having a carboxyl group, there are given, for example, imide compounds, such as 1-ethyl-3-(3-dimethylaminopropyl)carbodiimide (EDC) and N-hydroxysuccinimide (NHS). Those imide compounds may be used alone or in combination thereof. In at least one embodiment of the present invention, the electrode may be modified with the protein that specifically binds with the antibody of interest by, for example, bringing the protein that specifically binds with the antibody of interest into contact with the electrode (optionally having the self-assembled monolayer formed thereon). More specifically, the electrode may be modified with the protein that specifically binds with the antibody of interest by, for example, immersing the electrode in a suspension of the protein that specifically binds with the antibody of interest. In such embodiment, the concentration of the protein that specifically binds with the antibody of interest in the suspension is not particularly limited, but may be appropriately set within the range of, for example, from 0.01 mg/mL to 5 mg/mL, preferably from 0.1 mg/mL to 1 mg/mL. In addition, a period of time for which the electrode is immersed in the suspension is also not particularly limited, but may be appropriately set within the range of, for example, from 0.5 hour to 3 hours, preferably from 1 hour to 2 hours. A temperature in the step of immersing the electrode in the suspension is also not particularly limited, but may be appropriately set within the range of, for example, from 4° C. to 40° C., preferably from 10° C. to 40° C.

In at least one embodiment of the present invention, it is preferred that the electrode modified with the protein that specifically binds with the antibody of interest be brought into contact with a blocking agent to allow the blocking agent to adhere to the surface of the electrode in advance. Examples of the blocking agent include proteins (proteins that do not specifically bind with the antibody of interest), such as bovine serum albumin (BSA), casein, and skim milk. This case is preferred because the blocking agent adheres to the part of the surface of the electrode to which the protein that specifically binds with the antibody of interest is not bonded, with the result that, in the step of bringing the electrode into contact with wastewater to be described later, the antibody of interest in the wastewater can be suppressed from nonspecifically binding to the surface of the electrode itself instead of the protein that specifically binds with the antibody of interest. The step of bringing the blocking agent into contact with the electrode modified with the protein that specifically binds with the antibody of interest may be performed by immersing the electrode in a solution of the blocking agent. In such embodiment, the concentration of the blocking agent in the solution is not particularly limited, but may be appropriately set within the range of, for example, from 0.5% to 10%, preferably from 1% to 5%. In addition, a period of time for which the electrode is immersed in the solution of the blocking agent is also not particularly limited, but may be appropriately set within the range of, for example, from 0.5 hour to 2 hours, preferably from 1 hour to 1.5 hours. A temperature in the step of immersing the electrode in the suspension is also not particularly limited, but may be appropriately set within the range of, for example, from 4° C. to 30° C., preferably from 10° C. to 20° C.

In at least one embodiment of the present invention, first, the electrode modified with the protein that specifically binds with the antibody of interest, which has been prepared as described above, is brought into contact with wastewater. As a wastewater sample, one collected at a measurement location may be used as it is, or one appropriately diluted with water or the like may be used. For example, a sample having a protein concentration of from 0.001 ng/mL to 1,000 ng/mL may be used, and the protein concentration is preferably from 0.01 ng/mL to 10 ng/mL. The step of bringing an electrode modified with a protein that specifically binds with the antibody of interest into contact with wastewater may be performed by, for example, immersing the electrode modified with the protein that specifically binds with the antibody of interest in wastewater. In such embodiment, a period of time for which the electrode is immersed in the wastewater is not particularly limited, but may be appropriately set within the range of, for example, from 30 minutes to 90 minutes, preferably from 45 minutes to 75 minutes. A temperature in the step of immersing the electrode in the wastewater liquid is also not particularly limited, but may be appropriately set within the range of, for example, from 4° C. to 40° C., preferably from 10° C. to 25° C. Through this step, when the antibody of interest is present in the wastewater sample, the protein with which the surface of the electrode is modified and the antibody of interest are bound.

In at least one embodiment of the present invention, next, the step of bringing the electrode brought into contact with the wastewater in the above-mentioned step into contact with a reaction solution containing a redox substance is performed. Specifically, this step may be performed by, for example, lifting the electrode out of the wastewater and immersing the electrode in a reaction solution containing a redox substance. The redox substance is not particularly limited, but examples thereof include: a hexacyanidoferrate (II) ion and/or a hexacyanidoferrate(III) ion; an ethylenedi-amine-di(o-hydroxyphenylacetic acid) (EDDHA)-iron com-plex; a diethylenetriamine pentaacetic acid (DTPA)-iron complex; and salts thereof (e.g., potassium salts and sodium salts). The concentration of the redox substance in the reaction solution is not limited, but may be appropriately set within the range of, for example, from 1 mM to 10 mM, preferably from 2 mM to 5 mM. The reaction solution preferably has dissolved therein an electrolyte, such as sodium chloride, magnesium chloride, or calcium chloride. Those electrolytes may be used alone or in combination thereof. When the electrolyte is added, the concentration thereof is not limited, but may be appropriately set within the range of, for example, from 1 mM to 1,000 mM, preferably from 100 mM to 500 mM. As the reaction solution, there may be used one obtained by adding the redox substance and optionally the electrolyte and the like into a buffer, such as a phosphate buffer, a bicarbonate buffer, or a Tris hydrochloride buffer. The concentration of a buffer component is also not limited, but may be appro-priately set within the range of, for example, from 1 mM to 1,000 mM, preferably from 10 mM to 100 mM. The pH of the reaction solution may be appropriately set within the range of, for example, from 6 to 8, preferably from 6.5 to 7.5.

In addition, in at least one embodiment of the present invention, after the electrode has been lifted out of the wastewater and before the electrode is immersed in the reaction solution containing the redox substance, the surface of the electrode may be washed with a buffer (e.g., phos-phate-buffered saline (PBS)) or the like, followed by the removal of water on the electrode with a nitrogen gas or the like.

In at least one embodiment of the present invention, after the step of bringing the electrode into contact with a reaction solution containing a redox substance, the step including applying a voltage to the electrode in a state of being brought into contact with the reaction solution, and measuring a current is performed. In at least one typical embodiment of the present invention, in this step, not only the above-mentioned electrode, but also a counter electrode and a reference electrode are brought into contact with the reaction solution, and the electrode modified with the protein that specifically binds with the antibody of interest is used as a working electrode, to which the voltage is applied. A mate-rial for the counter electrode is not particularly limited, and examples thereof include a gold electrode, a platinum elec-trode, a diamond electrode, a palladium electrode, and a carbon electrode. Of those, a gold electrode or the like is preferred. In addition, a material for the reference electrode is also not particularly limited, and may be appropriately set depending on, for example, the range of the potential to be applied, but examples thereof include a silver electrode, a silver/silver chloride electrode, and a platinum electrode.

As a method of applying the potential, there are given, for example, cyclic voltammetry, squarewave voltammetry, linear sweep voltammetry, staircase voltammetry, and differential pulse voltammetry, and preferred examples thereof include cyclic voltammetry and squarewave voltammetry.

The range of the potential to be applied to the working electrode varies depending on, for example, the redox potential of the redox substance to be used, and is not particularly limited, but may be set within the range of, for example, from –0.5 V to 1.0 V, preferably from –0.3 V to 0.6 V with respect to the potential of a reference electrode made of silver (Ag). In a method, such as cyclic voltammetry or squarewave voltammetry, the lower limit of the potential to be applied to the working electrode (minimum potential) is not particularly limited, but may be set within the range of, for example, from –1.0 V to –0.1 V, preferably from –0.5 V to –0.3 V with respect to the potential of the reference electrode. The upper limit of the potential to be applied to the working electrode (maximum potential) is not particularly limited, but may be set within the range of, for example, from 0.1 V to 2.0 V, preferably from 0.5 V to 0.6 V with respect to the potential of the reference electrode. In a method involving performing a potential sweep, a sweep rate is not particularly limited, but may be set within the range of, for example, from 0.01 V/s to 0.5 V/s, preferably from 0.1 V/s to 0.2 V/s. In addition, a frequency in squarewave voltammetry or the like is not particularly limited, but for example, may be set within the range of, for example, from 1 Hz to 100 Hz, preferably from 5 Hz to 50 Hz. A period of time for which the potential is applied is also not particularly limited, but may be appropriately set within the range of, for example, from 1 second to 60 seconds, preferably from 5 seconds to 20 seconds. A temperature at the time when this step is performed is also not particularly limited, but may be appropriately set within the range of, for example, from 4° C. to 40° C., preferably from 10° C. to 25° C. Through this step, the redox substance in the reaction solution is oxidized/reduced through an electrode reaction on the surface of the working electrode, and a current corresponding thereto flows. Here, when the antibody of interest is present in the wastewater sample, the protein with which the surface of the working electrode is modified and the antibody of interest are specifically bound, and hence the area of an effective electrode surface where the redox substance can undergo the electrode reaction on the surface of the working electrode is reduced, with the result that the current that flows through the working electrode is reduced. Accordingly, through the current measurement in the above-mentioned step, the antibody of interest in the wastewater sample can be detected. In the method according to at least one embodiment of the present invention, the concentration of the antibody of interest in the wastewater sample can be measured in a simple manner by, for example, using a calibration curve, the calibration curve being prepared using a reference sample obtained by adding a known amount of the antibody to the wastewater sample, a blank sample (e.g., a wastewater sample in which the antibody was not detected), or the like.

According to at least one embodiment of the present invention, despite the use of the wastewater sample, which may contain many substances other than the antibody of interest, as a measurement sample, the antibody of interest in the sample can be detected. In addition, the method according to at least one embodiment of the present invention enables measurement by a simple method as compared to a method using a technology such as PCR, western blot, or SPR. Further, according to the method according to at least one embodiment of the present invention, measurement can be performed within a short period of time through squarewave voltammetry by immersing the electrode in the reaction solution, and hence real-time measurement can be performed. For example, although no time limitation is imposed on the real-time measurement, the concentration of the antibody of interest in the wastewater sample can be measured in real time in a simple manner within about several minutes to about several tens of minutes.

Kit for Detecting Antibody of Interest

According to at least one embodiment of the present invention, there is provided a kit for detecting an antibody of interest in wastewater, the kit including an electrode modified with a protein that specifically binds with the antibody of interest.

In this embodiment, the antibody of interest, the protein that specifically binds with the antibody, the electrode, the mode of the modification of the electrode with the protein, and the like are as described above. The kit according to at least one embodiment of the present invention may be used for the above-mentioned method according to at least one embodiment of the present invention for detecting an antibody of interest in wastewater.

The kit according to at least one embodiment of the present invention may include an electrolytic cell for use with the modified electrode. Current measurement may be performed by placing a reaction solution containing a redox substance in the electrolytic cell, inserting the electrode thereinto, and applying a voltage to the electrode. The kit according to at least one embodiment of the present invention may include, for example, a sample of the antibody of interest for reference. The kit according to at least one embodiment of the present invention may include the above-mentioned redox substance. In addition, the kit according to at least one embodiment of the present invention may further include water, a buffer, a buffer salt, a surfactant, a surface-active agent, a salt, a polysaccharide, or any other material to be generally used for bioassay so that electrode activity for wastewater sample analysis can be maintained for a long period of time. The kit may include a solvent, such as a water-soluble solvent, a water-insoluble solvent, or a water-soluble/water-insoluble solvent system. In addition, the kit according to at least one embodiment of the present invention may further include an instruction manual in which, for example, a procedure for carrying out the method according to at least one embodiment of the present invention is described.

Sensor for Detecting Antibody of Interest

According to at least one embodiment of the present invention, there is provided a sensor for detecting an antibody of interest in wastewater, the sensor including: a working electrode modified with a protein that specifically binds with the antibody of interest; and a counter electrode. The sensor according to at least one embodiment of the present invention may be used for the method according to at least one embodiment of the present invention for detecting an antibody of interest in wastewater.

In this embodiment, the antibody of interest, the protein that specifically binds with the antibody, the electrode, the mode of the modification of the electrode with the protein, and the like are as described above. In addition, in at least one preferred embodiment, the sensor of the present invention may further include a reference electrode. In at least one preferred embodiment of the present invention, there may be used a tripolar electrode including: a substrate; and a working electrode, a reference electrode, and a counter electrode that are arranged on the substrate. The arrangement of the electrodes is not limited, but for example, a configuration shown in FIG. 4 may be adopted. The sensor may be used by being connected to an electrochemical analyzer having the functions of a potentiostat, a function generator, and the like.

A certain embodiment of the present invention is specifically described below by way of Example. However, the present invention is not limited to Example described below. Analysis System for Detecting Antibody of Interest According to at least one embodiment of the present invention, there can be provided an analysis system configured to detect an antibody of interest in wastewater by the above-mentioned method. In addition, there can be provided an analysis system configured to measure a concentration of the antibody of interest in a wastewater sample in real time.

Example

Method

Electrochemical measurement was performed using an electrochemical analyzer having the functions of a potentiostat, a function generator, and the like (Model 760EH, BAS) and its control software (see an electrochemical analyzer system of FIG. 1). A to D in FIG. 1 are as follows:

A: electrochemical analyzer (potentiostat+function generator)

B: Faraday cage (removal of noise due to an air flow or the like)

C: measurement software (control of the electrochemical analyzer)

D: measurement cell

Electrodes/Screen-printed Gold Electrode (SPGE)

Working electrode and counter electrode: gold (WE: 4 mm diameter)

Reference electrode: silver

Measurement solution/2.5 mM phosphate buffer (pH 7.4) containing 4 mM potassium hexacyanidoferrate(III) and 0.1 M sodium chloride $[Fe(CN)_6]^{3-}+e^- \leftrightarrows [Fe(CN)_6]^{4-}$ Seiya HIRANO et al (2020)

For electrodes, there was used a screen-printed gold electrode (SPGE) (Dropsens) including a working electrode and counter electrode made of gold, and a reference electrode made of silver, in which the working electrode had a diameter of 4 mm. As a measurement solution, there was used a solution (pH 7.4) obtained by dissolving 4 mM potassium hexacyanidoferrate(III) and 0.1 M (1.0 M) sodium chloride serving as an electrolyte in 2.5 mM (25 mM) phosphate buffer in order to use redox behavior between a hexacyanidcferrate(II) ion and a hexacyanidoferrate(III) ion, which is widely used in electrochemical measurement. Measurement was performed with an electrode cell, made up of the electrodes and the measurement solution, being placed in the Faraday cage in order to reduce noise due to an air flow or the like.

An electrode modification method is as described below. That is, after the surface of the SPGE had been rinsed with ultrapure water, first, in order to produce a self-assembled monolayer (SAM) of a carboxylic acid on the surface of the electrode through gold-thiol bonding, the electrode was immersed in a 5 mM MUA/MPA (7:3, v/v) ethanol solution, and the whole was left at rest at room temperature overnight. After that, the surface of the electrode was washed with ethanol, and water on the surface was removed with a $N_2$ gas. Next, in order to bond a terminal carboxy group and a primary amine of an antibody to each other through a carbodiimide crosslinking reaction, 10 μL of a 400 mM EDC and 100 mM NHS solution was dropped onto the Au-MPA/MPA electrode, and the whole was left at rest at room temperature for 1 hour. After that, the surface of the electrode was washed with ultrapure water, and water on the surface was removed with a $N_2$ gas. Subsequently, in order to immobilize an anti-human IgA antibody on the surface of the working electrode, 10 μL of a 0.5 mg/mL anti-human IgA antibody (solvent: PBS) was dropped onto the Au-MUA/MPA (EDC/NHS) electrode, and the whole was left at rest in an incubator at 37° C. for 1.5 hours. After that, the surface of the electrode was washed with PBS, and water on the surface was removed with a $N_2$ gas. Further, in order to suppress the binding of human IgA to an unreacted carboxy group and a nonspecific site, 10 μL of a 1% bovine serum albumin (BSA) solution (solvent: PBST) was dropped onto the Au-MUA/MPA (EDC/NHS)-IgG electrode, and the whole was left at rest at room temperature for 1 hour.

Figure 2:
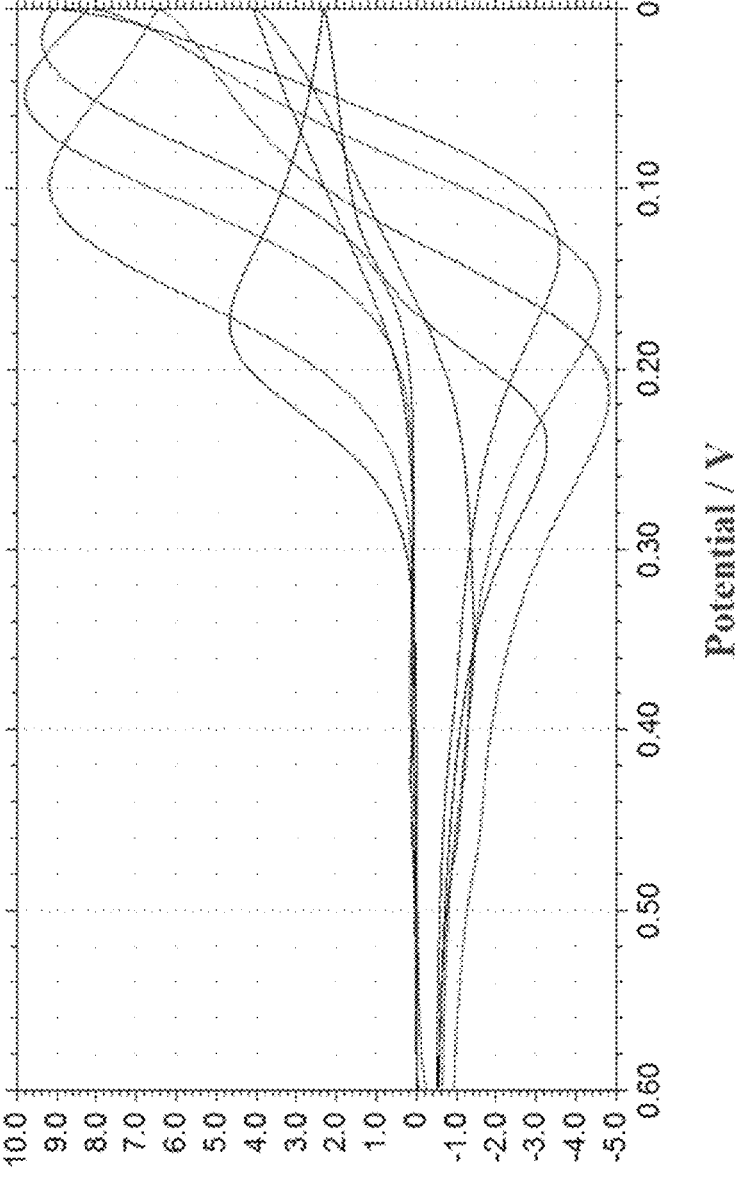
FIG. 2 shows measurement results of cyclic voltammetry in an electrode modification process in Example. I. SAM production. II. NHS esterification of terminus. III. Anti-human IgA immobilization. IV. Suppression treatment. V. Gold electrode. Initial potential [V]: 0.6, maximum potential [V]: 0.6, minimum potential [V]: 0, sweep rate [V/s]: 0.1, sensitivity [A/V]: $1 \times 10^{-5}$

Cyclic voltammetry was performed at each stage of modification described above. The results are shown in FIG. 2. The range of a potential applied to the working electrode is from −0.3 V to 0.6 V, and a sweep rate is 0.1 V/s. However, FIG. 2 only shows experimental results in the potential range of from 0 V to 0.6 V. As a result, as compared to the unmodified electrode, there were observed a decrease in peak current after the production of the SAM, an increase in peak current after the NHS esterification of the terminal carboxy group, and decreases in peak current caused by the subsequent anti-human antibody immobilization and suppression treatment, indicating that the anti-human antibody was immobilized on the surface of the electrode as expected.

Figure 3:
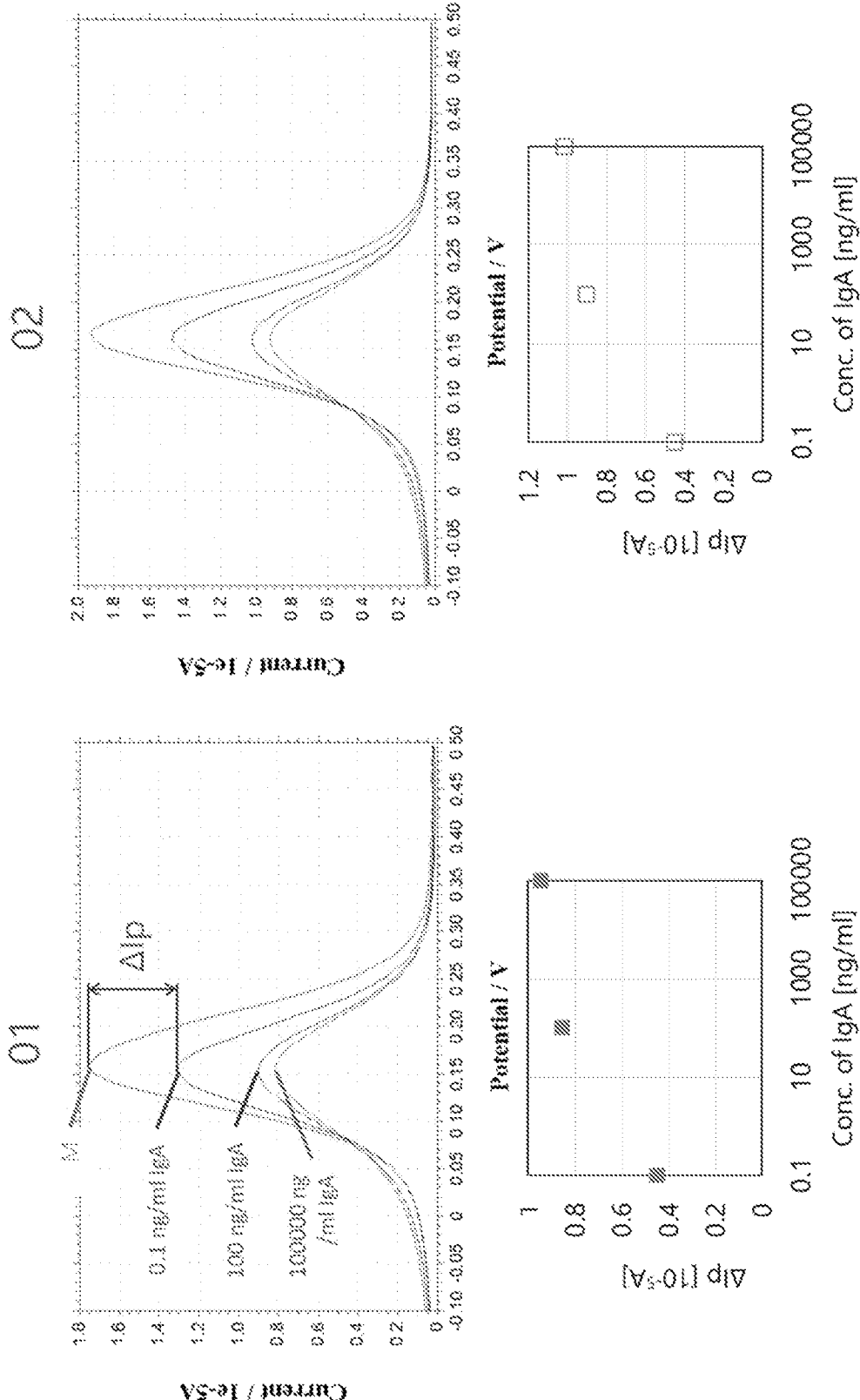
FIG. 3 shows results of preparation of a calibration curve for a human antibody in wastewater with an electrochemical sensor in Example. This was performed with two identical electrodes produced in order to determine reproducibility (left: first time, right: second time). Upper left graph of FIG. 3: electrode 01. Upper right graph of FIG. 3: electrode 02. M: modified electrode.

After the electrode modification, human IgA dispersed in a wastewater supernatant was dropped so as to cover the surface of the working electrode having the anti-human IgA antibody immobilized thereon, and the whole was left at rest at 37° C. for 1 hour to promote an antigen-antibody reaction. After that, the surface of the electrode was washed with a phosphate buffer, and squarewave voltammetry was performed to give results of FIG. 3. The range of a potential applied to the working electrode was set to from −0.1 to 0.5 V. The results are shown in FIG. 3. Although not shown in FIG. 3, a frequency was set to 10 Hz, a potential increment for each step was set to 0.004 V, and an amplitude was set to 0.005 V. As a result, a calibration curve was successfully drawn with good reproducibility in the range of from 0.1 ng/mL to 100,000 ng/mL.

Thus, in at least one embodiment of the present invention, despite the use of the wastewater sample, which may contain many substances other than the antibody of interest, as a measurement sample, the antibody of interest in the sample was able to be detected. In addition, the method determined in this Example enabled measurement by a simple method as compared to a method using a technology such as PCR, western blot, or SPR. Further, measurement can be performed within a short period of time by immersing the modified electrode in the wastewater sample and performing, for example, squarewave voltammetry, and hence real-time measurement can be performed.

What is claimed is:

1. A method of detecting an antibody of interest as an infectious disease marker in wastewater, the method comprising:

bringing an electrode, modified with a protein that specifically binds with the antibody of interest as the infectious disease marker, into contact with the wastewater;

lifting the electrode out of the wastewater;

bringing the electrode, which has been lifted out of the wastewater, into contact with a reaction solution containing a redox substance; and applying a voltage to the electrode in a state of being in contact with the reaction solution, and measuring a current, wherein, in the bringing the electrode into contact with the wastewater, the protein with which a surface of the electrode is modified and the antibody of interest are bound.

2. The method according to claim 1, wherein the antibody of interest is one of an antiviral antibody, an antibacterial antibody, an antiprotozoal antibody, or an anti-tumor cell antibody.

3. The method according to claim 1, wherein the protein that specifically binds with the antibody of interest is one of an antibody that specifically binds to the antibody of interest or an antigen protein to which the antibody of interest specifically binds.

4. The method according to claim 1, wherein the electrode is modified with the protein that specifically binds with the antibody of interest via a self-assembled monolayer.

5. A kit for detecting an antibody of interest in wastewater by the method of claim 1, the kit comprising the electrode, modified with the protein that specifically binds with the antibody of interest.

6. A sensor for detecting an antibody of interest in wastewater by the method of claim 1, the sensor comprising:

the electrode, modified with the protein that specifically binds with the antibody of interest; and a counter electrode.

7. An analysis system configured to detect an antibody of interest in wastewater by the method of claim 1.

8. The analysis system according to claim 7, wherein the analysis system is configured to measure a concentration of the antibody of interest in a wastewater sample in real time.

9. The method according to claim 1, wherein, in the applying the voltage to the electrode and measuring the current, when the antibody of interest is present in a wastewater sample, the protein with which the surface of the electrode is modified and the antibody of interest are specifically bound, and an area of an effective electrode surface where the redox substance can undergo an electrode reaction on the surface of the electrode is reduced such that the current that flows through the electrode is reduced.

10. A method of detecting an antibody of interest as an infectious disease marker in wastewater, the method comprising:

bringing an electrode, modified with a protein that specifically binds with the antibody of interest, into contact with the wastewater;

bringing the electrode into contact with a reaction solution containing a redox substance; and applying a voltage to the electrode in a state of being in contact with the reaction solution, and measuring a current, wherein the redox substance is at least one kind selected from the group consisting of: a hexacyanidoferrate(II) ion and/or a hexacyanidoferrate(III) ion; an EDDHA-iron complex; a DTPA-iron complex; and salts thereof.

\*   \*   \*   \*   \*